(12) United States Patent
Chan et al.

(10) Patent No.: US 7,419,580 B2
(45) Date of Patent: Sep. 2, 2008

(54) METHODS AND APPARATUS FOR THE OXIDATION OF GLUCOSE MOLECULES

(75) Inventors: Kwong-Yu Chan, Pokfulam (HK); Xin Zhang, Guangdong (CN); Chung Man Lam, Shakeiwan (HK); Alfred C. C. Tseung, London (GB); Pei Kang Shen, Ha ngzhou (CN); Jin Kua You, Xiamen (CN)

(73) Assignee: The University of Hong Kong, Hong Kong (HK)

( * ) Notice: Subject to any disclaimer, the term of this patent is extended or adjusted under 35 U.S.C. 154(b) by 1374 days.

(21) Appl. No.: 09/996,120

(22) Filed: Nov. 28, 2001

(65) Prior Publication Data
US 2002/0125146 A1    Sep. 12, 2002

Related U.S. Application Data

(60) Provisional application No. 60/255,608, filed on Dec. 14, 2000.

(51) Int. Cl.
  *C25C 1/00* (2006.01)
  *C25B 3/00* (2006.01)
(52) U.S. Cl. .................. 205/413; 205/343; 205/427; 205/455
(58) Field of Classification Search ............. 568/959; 205/343, 427, 455, 293, 413; 204/293, 403.01; 429/218.1
See application file for complete search history.

(56) References Cited

U.S. PATENT DOCUMENTS 3,160,526 A * 12/1964 Ruetschi .................. 429/347
3,668,014 A * 6/1972 Katsoulis et al. .............. 429/42
4,126,934 A * 11/1978 Richter et al. .............. 29/623.1
4,294,891 A   10/1981 Yao et al. ........................ 429/2
4,297,195 A * 10/1981 Sato et al. .............. 204/290.09

(Continued)

FOREIGN PATENT DOCUMENTS

| CN | 1247909 | 3/2000 |
|---|---|---|
| JP | 10160700 | 6/1998 |
| WO | WO 9837997 A2 * | 9/1998 |

OTHER PUBLICATIONS

Barbe et al., "Nanocrystalline Titanium Oxide Electrodes for Photovoltaic Applications", J. Am. Ceram. Soc. (no month, 1997), vol. 80, No. 12, pp. 3157-3171.*

(Continued)

*Primary Examiner*—Edna Wong
(74) *Attorney, Agent, or Firm*—Jones Day

(57) ABSTRACT

A catalyst comprising Pt—Co alloy, or Pt—Co—Sn alloy or Pt—$Co_mO_n$ mixed metal oxides is disclosed to be used as a catalyst for the direct electrochemical oxidation of glucose or other simple sugars and carbohydrates at room temperature. The catalyst can be supported on metal electrodes, graphite electrodes, porous carbon electrodes, or gas diffusion electrodes. An electrode containing this catalyst will be used as the key component in a direct glucose-air fuel cell operating in alkaline media with a good room temperature performance. This catalyst can also be applied as a key electrode material in a glucose sensor to detect glucose concentration in neutral or alkaline medium. The preparation method of the catalyst, optimum composition, and results of glucose sensor and glucose fuel cell applications are disclosed.

21 Claims, 13 Drawing Sheets

U.S. PATENT DOCUMENTS

| | | | |
|---|---|---|---|
| 4,447,506 A | | 5/1984 | Luczak et al. ............... 429/44 |
| 4,867,909 A | | 9/1989 | Babinec et al. ............. 252/518 |
| 4,937,058 A | * | 6/1990 | Dupin et al. ................ 423/224 |
| 5,536,379 A | * | 7/1996 | Nonaka et al. .............. 204/284 |
| 5,538,811 A | * | 7/1996 | Kanbara et al. ............. 429/307 |
| 5,660,940 A | | 8/1997 | Larsson et al. ............... 429/13 |
| 5,876,867 A | | 3/1999 | Itoh et al. .................... 429/44 |
| 5,976,719 A | | 11/1999 | Kim et al. ...................... 429/2 |

OTHER PUBLICATIONS

G.G. Neuburger, D.C. Johnson, Pulsed Amperometric Detection of Carbohydrates at Gold Electrodes with a Two-Step Potential Waveform, , Anal. Chem., 59 (1987) 150-154, no month.

I.T. Bae, X. Xing, C.C. Liu, and E. Yeager, J. Electroanal. In situ Fourier Transform Infrared Reflection Absorption Spectroscopic Studies of Glucose Oxidation on Platinum in Acid, Chem., 284 (1990) 335-349, no month.

Y.B. Vassilyev, O.A. Khazova, and N.N. Nikolaeva, J. Electroanal. Kinetics and Mechanism of Glucose Electrooxidation on Different Electrode-Catalysts, Chem., 196 (1985) 105-125, no month.

S.V. Prabhu and R.P. Baldwin, Constant Potential Amperometric Detection of Carbohydrates at a Copper-Based Chemically Modified Electrode, Anal. Chem., 61 (1989) 852-856, no month.

J. Wang and Z. Taha, Catalytic Oxidation and Flow Detection of Carbohydrates at Ruthenium Dioxide Modified Electrodes, Anal. Chem., 62 (1990) 1413-1416, no month.

R.F. Reim and R.M. Van Effen, Determination of Carbohydrates by Liquid Chromatography with Oxidation at a Nickel(III) Oxide Electrode, Anal. Chem., 58 (1986) 3203-3207, no month.

L.M. Santos and R.P. Baldwin, Electrochemistry and Chromatographic Detection of Monosaccharides, Disaccharides, and Related Compounds at an Electrocatalytic Chemically Modified Electrode, Anal. Chim. Acta, 206 (1988) 85-96, no month.

J. Zhou and E. Wang, Sensitive Amperometric Detection of Glucose by Reversed Phase Liquid Chromatography at a Prussian Blue Chemically Modified Electrode of Novel Construction, J. Electroanal. Chem., 331 (1992) 1029-1043, no month.

X. Zhang, K.Y. Chan, and A.C.C. Tseung, Electrochemical Oxidation of Glucose by Pt/WO3 Electrode, J. Electroan. Chem., 386 (1995) 241-243, no month.

X. Zhang, K.Y. Chan, J.K. You, Z.G. Lin, and A.C.C. Tseung, Partial Oxidation of Glucose by a PT WO3 Electrode, J. Electroan. Chem., 430 (1997) 147-153, no month.

B. Wan and A.C.C. Tseung, Some Studies Related to Electricity Generation from Biological Fuel Cells and Galvanic Cells, in vitro and in vivo, Medical and Biol. Eng. Jan (1974) 14-28, no month.

T. Chen, S.C. Barton, G. Binyamin, Z. Gao, Y. Zhang, H-H Kim, and A. Heller, A Miniature Biofuel Cell, J. Am. Chem. Soc., 123 (2001) 8630-8631, no month.

J.C. Amphlett, B.A. Peppley, E. Halliop, and A. Sadiq, The Effect of Anode Flow Characteristics and Temperature on the Performance of a Direct Methanol Fuel Cell, J. Power Sources, 96 (2001) 204-213, no month.

S.P. Jiang, Y.Z. Chen, J.K. You, T.X. Chen, and A.C.C. Tseung, Reactive Deposition of Cobalt Electrodes, J. Electrochem. Soc. 137 (1990) 3374-3380, no month.

PCT International Search Report dated Mar. 28, 2002 (3 pgs.).

* cited by examiner

US 7,419,580 B2

METHODS AND APPARATUS FOR THE OXIDATION OF GLUCOSE MOLECULES

This application claims the benefit of U.S. Provisional Application No. 60/255,608 filed Dec. 14, 2000.

FIELD OF THE INVENTION

The present invention relates to the field of inorganic catalysts, and the use of such catalysts in the oxidation of organic molecules.

BACKGROUND OF THE INVENTION

Electrochemical oxidation of glucose has been studied for the potential applications as a detector for dissolved glucose in blood or other media. Current commercial blood glucose sensors use an enzyme electrode to oxidize glucose, which is followed with an indirect electrochemical detection of the enzymatic reaction products. Enzyme is relatively expensive, with a limited shelf-life, a low tolerance to elevated temperature, and it is not suitable for industrial applications. Glucose oxidase and glucose hydrogenase were the common enzymes to be immobilized in electrodes and to have selective reactions with glucose in a solution. Inorganic catalyst materials have the advantages of direct electrochemical oxidation, a longer shelf-life, and are resistant to the high temperatures and other harsh operating conditions found in a bioreactor or other industrial applications. The previous investigated materials of inorganic electrocatalysts include platinum, gold, ruthenium, iridium, their mixtures, and their oxides. A high oxidation potential was required to oxidize glucose and the current density was low, thus unfavorable for practical devices of glucose oxidation.

Although the theoretical concept of using glucose to power a bio-fuel cell has been mentioned in the past, a workable glucose-air fuel cell has not been demonstrated due to poor performance of the previously tested catalysts which include enzymes. The previous power densities reported were in the orders of microwatts per square centimeters. Glucose is inexpensive, safe, commonly available, conveniently stored, non-toxic, and hazard free. It offers certain advantages over the common fuels considered for portable fuel cells, such as hydrogen, methanol, and borohydride.

In U.S. Pat. No. 5,660,940, a biofuel-powered fuel cell is described with glucose, arabinose, and other carbohydrates as possible fuels. The fuel cell operates at above 90 ° C. with a two-step oxidation process using platinum, ruthenium, and vanadium as catalysts. In U.S. Pat. No. 5,976,719, a biofuel cell is described with glucose as a possible fuel. The oxidation is indirect and requires a microorganism to react with the glucose to generate other species to power the fuel cell. In U.S. Pat. No. 4,294,891, an implantable bio-oxidant fuel cell is described using glucose as a fuel and platinum, ruthenium, rubidium, iridium, nickel as catalysts for the anode. The power generated was in microwatts range. In U.S. Pat. No. 4,447,506, a ternary fuel cell catalyst containing platinum, cobalt, and chromium was disclosed for use as cathode material for oxygen reduction in acid medium, but not to be used as an anode.

SUMMARY OF THE INVENTION

This invention provides the composition of a catalyst that allows direct electrochemical oxidation of organic molecules, including carbohydrates and short chain alcohols. This invention further provides the composition of a catalyst that allows direct electrochemical oxidation of dissolved glucose in neutral and alkaline media, with a very low oxidation potential and moderate to high current density. The methods of preparing this catalyst into a working electrode are described by examples. The application of this invention is demonstrated by a room temperature direct glucose-air fuel cell having an open circuit voltage of 1.08 V and a peak power density of 3 $mW/cm^2$. Other organic molecule based fuels like arabinose, mannitol, galactose, mannose, sorbitol, xylose, methanol, and ethanol can also power the fuel cell with different power densities. In another example, the application of this invention for detecting dissolved glucose under physiological conditions is also shown.

DETAILED EMBODIMENT OF THE INVENTION

Figure 1A:
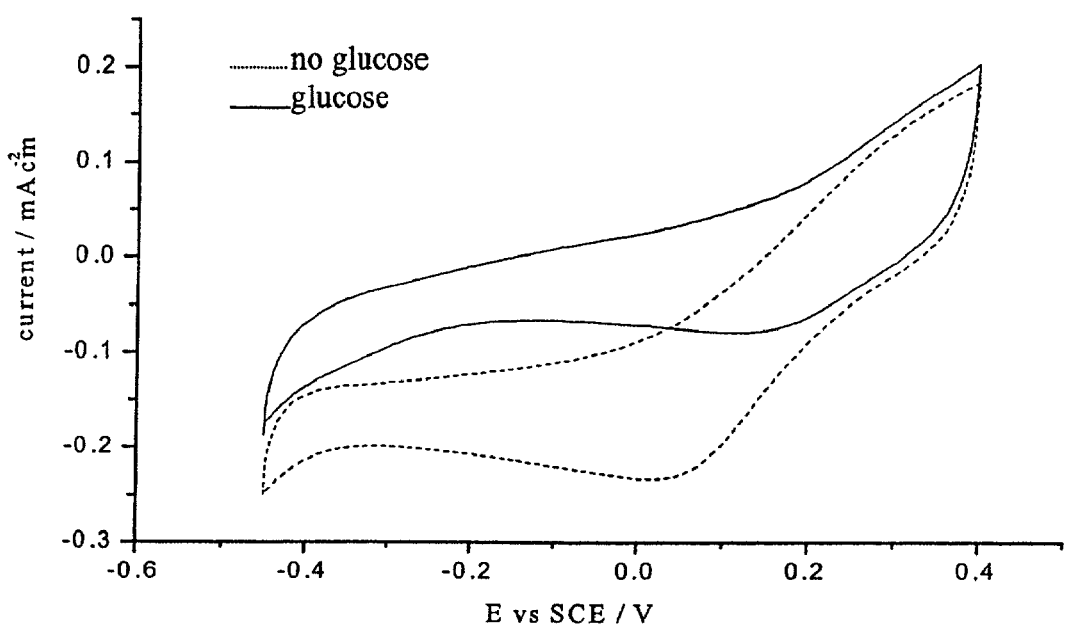
FIG. 1(a) is a cyclic voltammogram of a Pt wire electrode in 0.016 molar glucose in a pH 7.4 buffer solution.

This invention discloses a combination of electrode materials that can electrochemically oxidize organic molecules. This invention further discloses a combination of electrode materials that can electrochemically oxidize glucose at a very low potential and with a high current density. The low oxidation potential of glucose allows the development of an inorganic glucose sensor with minimum interferences from other dissolved constituents. The use of an inorganic electrocatalysts as described in this invention will not have the disadvantages noted above for current commercial blood glucose sensors. The use of such an electrocatalyst for detecting dissolved glucose in neutral buffer can be demonstrated.

The effectiveness of the present invention can be demonstrated by using a small direct glucose-air alkaline fuel cell with a single cell open circuit voltage (OCV) of 1.08 V and a power density of 3 mA/cm$^2$, operating at room temperature. At room temperature, this OCV exceeds those practically achieved for a methanol-air fuel cell, the primary contender for commercial small scale fuel cells. With the application of the electrocatalyst in this invention, the use of glucose as a power source for portable consumer electronics devices is possible. The use of glucose as a fuel has many advantages when compared to such fuels as hydrogen, methanol, and borohydride. Glucose is inexpensive, commonly available, conveniently stored, safe, non-toxic, and hazard free. The theoretical energy per volume for glucose is the highest if compared to methanol and hydrogen and has a good potential for micro or small scale fuel cells.

The use of precious metals such as platinum, gold, ruthenium, rhodium, iridium, and their alloys and oxides as electrocatalysts for electrochemical oxidation of glucose has generally been reported for acidic, neutral, and alkaline media. The motivation of previous studies was to develop an electrode for electrochemical detection of glucose. A glucose-air fuel cell had not been conceived to be practical. The problems of these electrocatalysts, as listed in TABLE 1, is their high oxidation potentials and low current densities, in other words, the low catalytic activity of the metals and their combination for electrooxidation of glucose.

This invention discloses that by adding cobalt or its oxides to platinum, the activity for glucose oxidation can be markedly increased in alkaline and neutral media. As shown also in TABLE 1, the oxidation potential is as low as −0.8 V /Hg/HgO with an oxidation current of 5 mA/cm$^2$ in the alkaline medium. This provides the possibility of a room temperature direct glucose-air fuel cell which in the past had not been demonstrated. The role of cobalt is related to its multiple oxidation states and its bi-functional character of oxidizing intermediates like carbon monoxide and carbonyl function groups.

The comparison of the glucose-air fuel cells and other glucose-oxygen fuel cells reported in the literature are shown in TABLE 2. Most of the reported data are intended for implantable and biofuel cell applications. The power densities obtained using platinum black or enzyme electrodes were only in microwatts per sq. cm as opposed to the 3 mW/cm$^2$ value obtained in this invention.

Figure 1B:
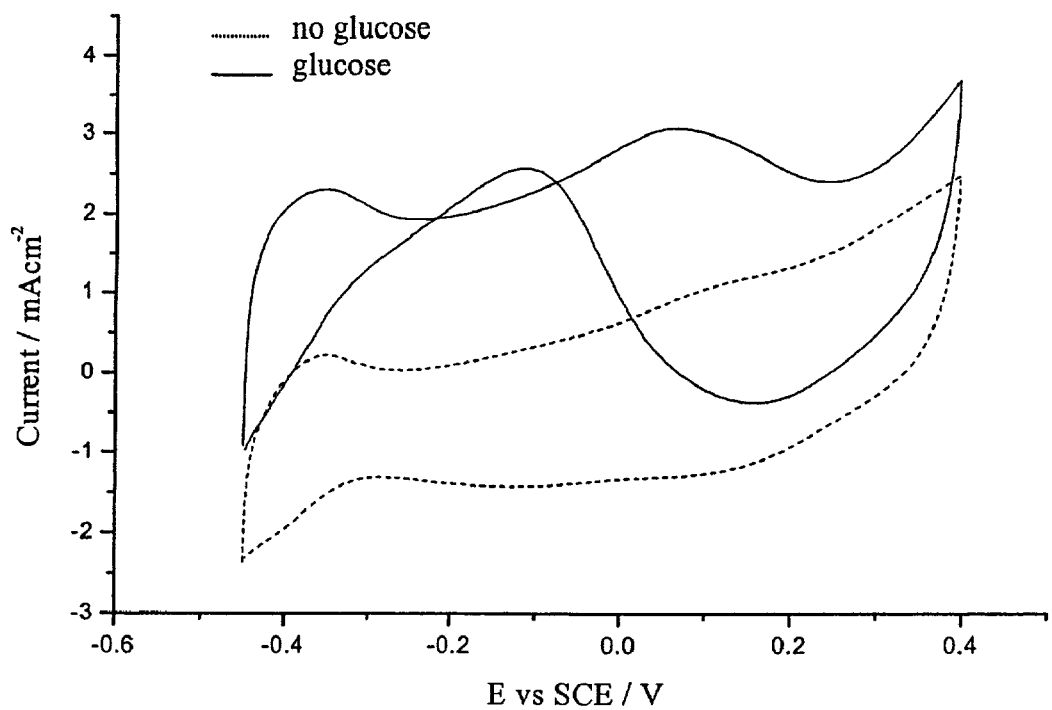
FIG. 1(b) is a cyclic voltammogram of a $Pt/Co/Co_3O_4$ deposited wire electrode in 0.016 molar glucose in a pH 7.4 buffer solution.
Figure 2:
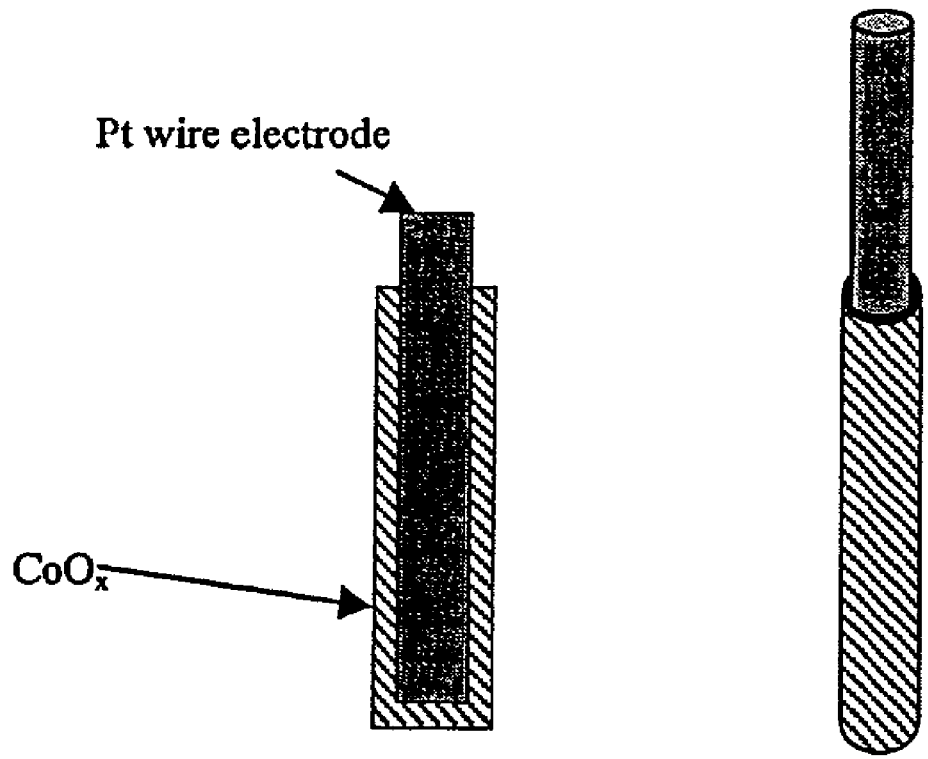
FIG. 2 is a schematic representation of a Pt-wire electrode with a layered catalyst.

The increase in activity of the PtCo alloy can be demonstrated by comparing the cyclic voltammograms of glucose on a platinum electrode and a platinum/cobalt/cobalt oxide electrode in a phosphate buffer, as is shown in FIGS. 1(a) and 1(b). In FIG. 1(a), the cyclic voltammogram is shown for a Pt wire electrode in phosphate buffer (pH 7.4) at 10 mVsec$^{-1}$ in a solution with 0.016 M glucose and without glucose. As seen in FIG. 1(a), a low activity for platinum is shown for glucose oxidation. In FIG. 1(b), the cyclic voltammogram is shown for a Pt/Co/Co$_3$O$_4$ deposited wire electrode in phosphate buffer (pH 7.4) at 10 mV sec$^{-1}$ in a solution with 0.016 M glucose and without glucose. A schematic representation of such an electrode is shown in FIG. 2. As seen in FIG. 1(b), a twenty times increase in the peak current density is observed at a potential of −0.4 V/SCE for the oxidation of glucose on Pt/Co/Co$_3$O$_4$ in a neutral buffer solution.

Figure 3:
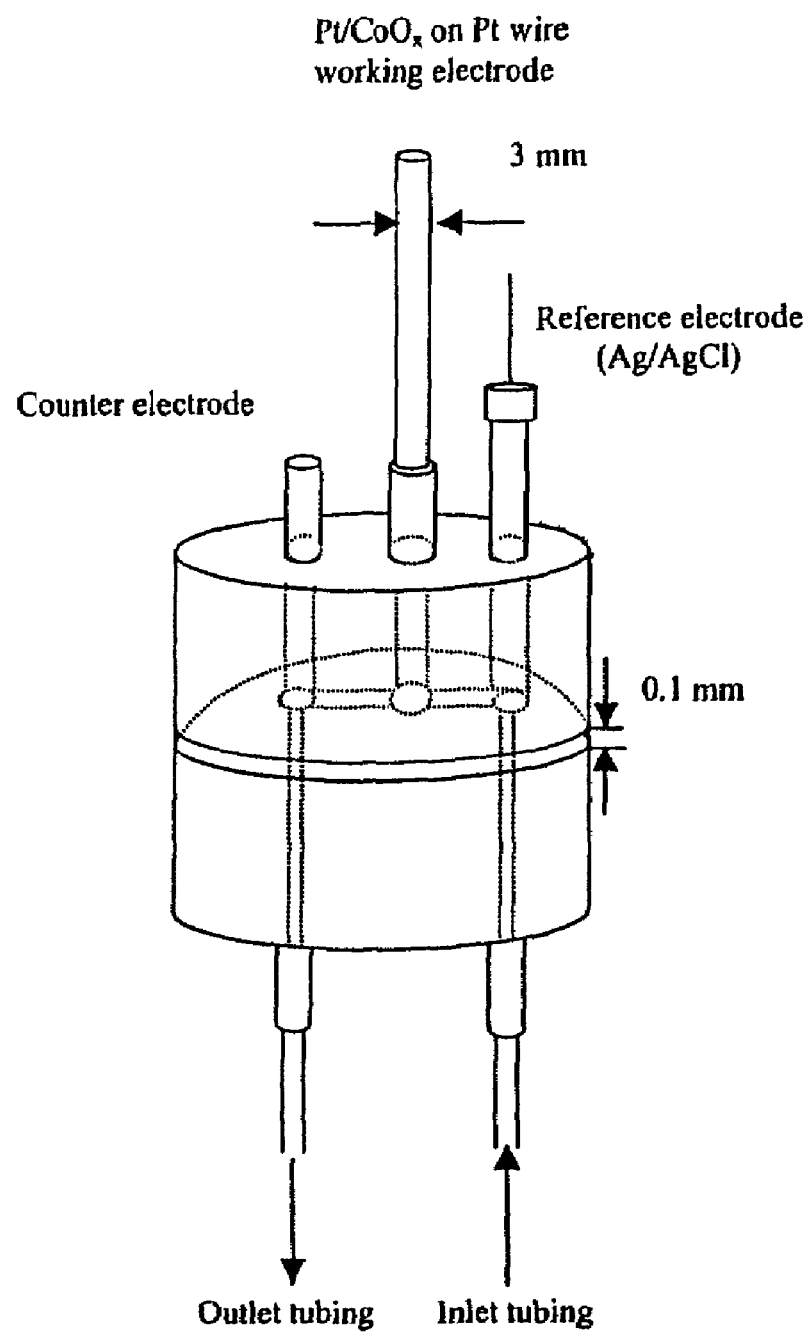
FIG. 3 is a schematic representation of a flow injection analysis cell.
Figure 4:
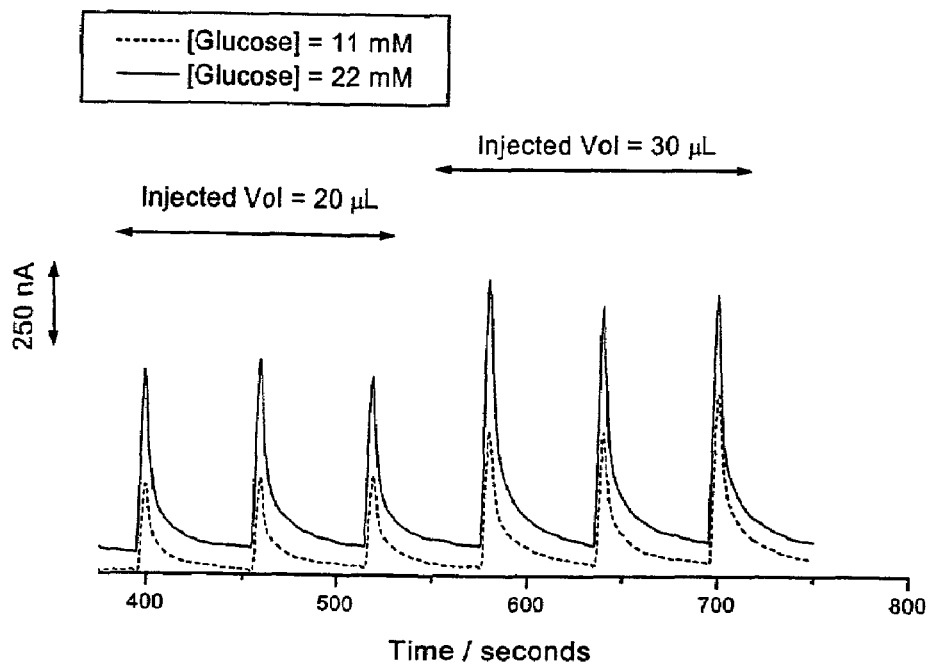
FIG. 4 is a graph showing the oxidation current transient response to glucose injection in a flow injection analysis.
Figure 5:
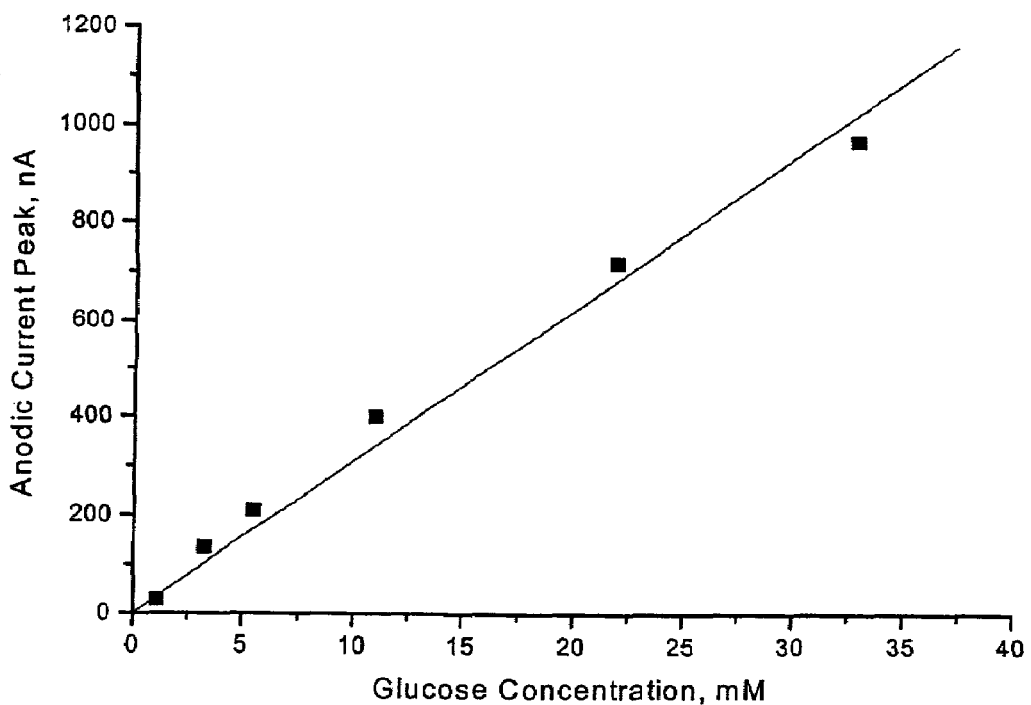
FIG. 5 is a graph showing the peak current in FIA versus glucose concentration.

The applicability of such an electrocatalyst as a glucose sensor is demonstrated in a flow injection analysis setup like the one shown in the schematic diagram in FIG. 3. The applied oxidation potential is 0.250 V vs Ag/AgCl. FIG. 4 shows the oxidant current transient response to glucose injection in a flow injection analysis experiment. The sensitivity and repeatability of the oxidation peak current is demonstrated in FIG. 4 by the series of oxidation current peaks in response to corresponding injections of dissolved glucose of different concentrations. A platinum wire with platinum, cobalt and cobalt oxides deposited was used as the sensing electrode. In FIG. 5, the corresponding dynamic linear response range for the glucose concentration is shown. FIG. 5 shows the peak current in FIA versus glucose concentration.

Figure 6:
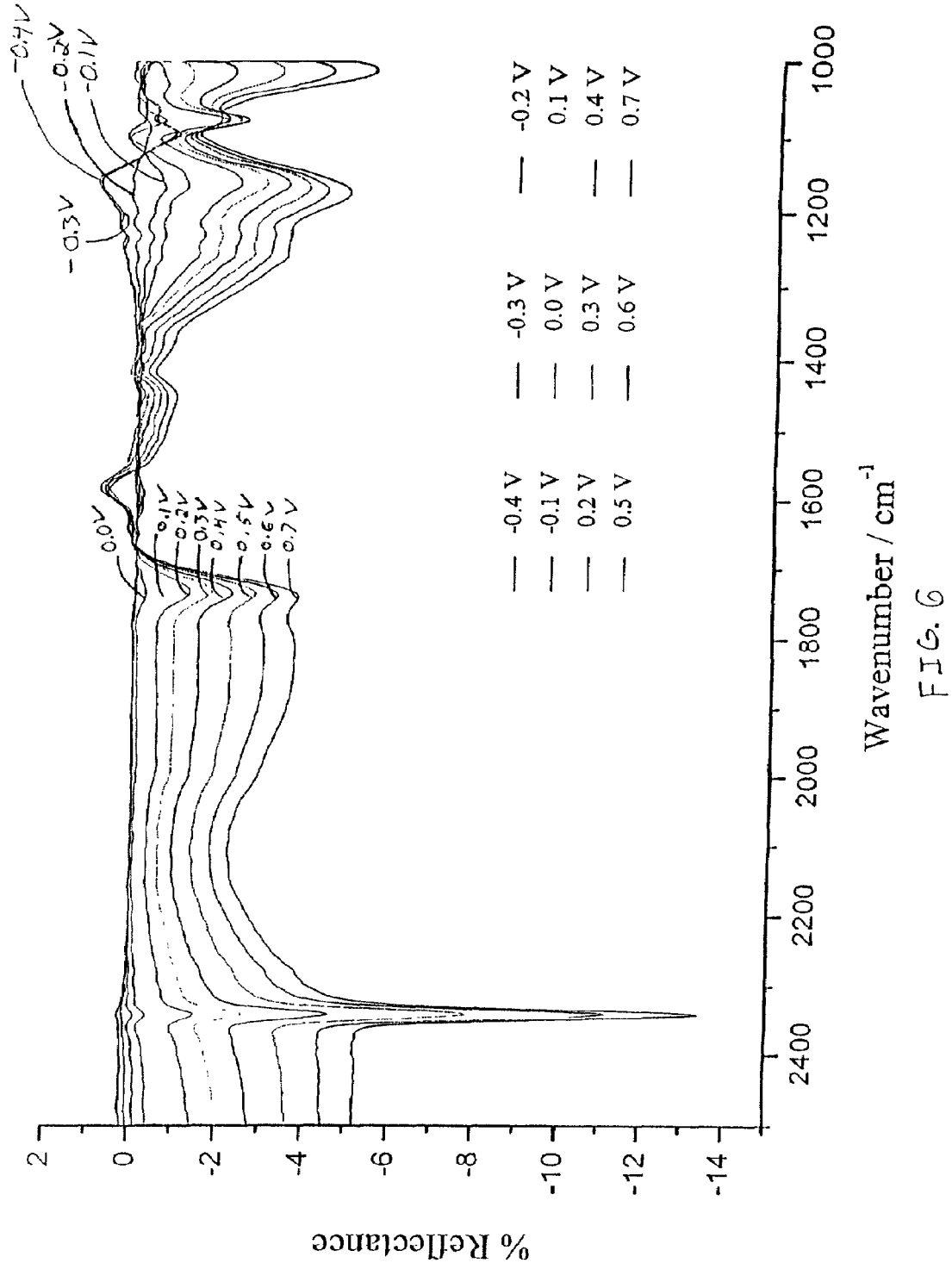
FIG. 6 is a graph showing an in-situ FTIR for 0.15 M glucose oxidation on $Pt/Co/Co_3O_4$ in a pH 7.4 phosphate buffer.

The intermediate products of direct glucose oxidation with Pt/Co/Co$_3$O$_4$ in a pH 7.4 phosphate buffer were identified by in-situ Fourier transform infra red spectroscopy (FTIR). FIG. 6 shows an in-situ FTIR-RAS for 0.15 M glucose oxidation on Pt/Co/Co$_3$O$_4$ in a pH 7.4 phosphate buffer. As shown in FIG. 6, the product clearly identified was carbon dioxide 2342 cm$^{-1}$ and an intermediate product gluconolactone at 1744 cm$^{-1}$ was also detected.

Figure 7:
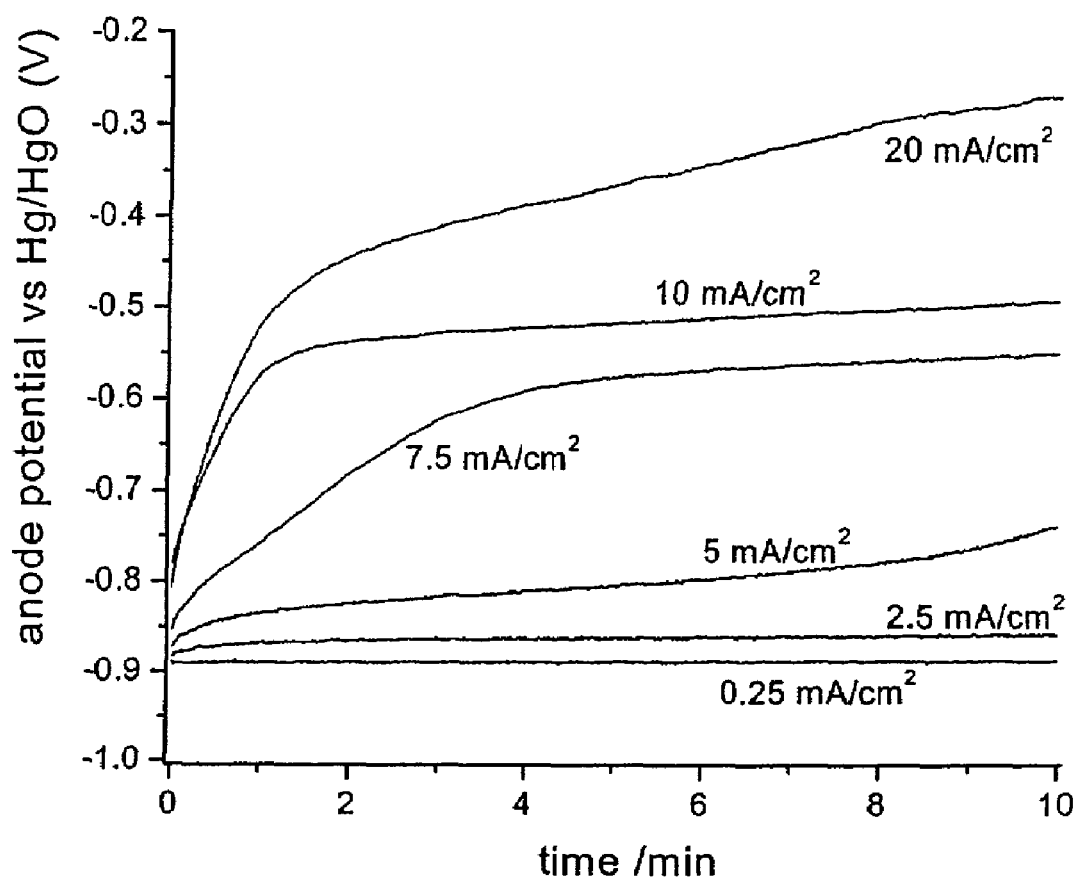
FIG. 7 is a graph showing the anode performance during oxidation of 0.5 M glucose in 0.5 M NaOH at 20° C.
Figure 8:
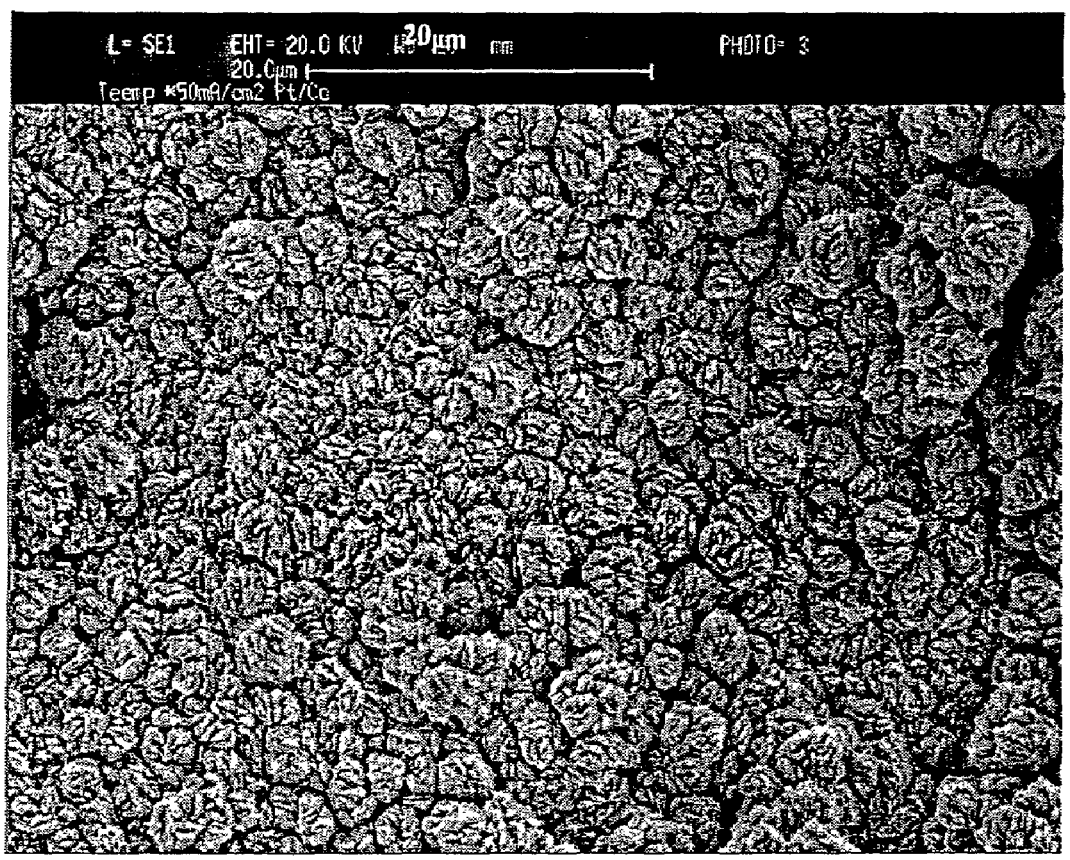
FIG. 8 is a scanning electron micrograph of a Pt/Co/C electrode surface.

For fuel cell applications, the steady-state direct electrochemical oxidation of glucose on high surface area electrodes is demonstrated by chronopotentiometry as shown in FIG. 7. The glucose solution is 0.5 molar in a 0.5 molar NaOH solution and the temperature is 20° C. The 0.283 cm$^2$ anode electrode for the half-cell studies is a carbon electrode deposited with platinum and cobalt. FIG. 8 shows the scanning electron micrograph of a Pt/Co/C electrode surface. The scan electron micrograph of the surface of the electrode and corresponding energy dispersive x-ray (EDX) analyses showed 14.5% atom cobalt and 85% atom platinum. The applicability to a direct glucose-air fuel cell can be inferred from the results in FIG. 7 and the well documented air cathode half-cell performance data.

Figure 9:
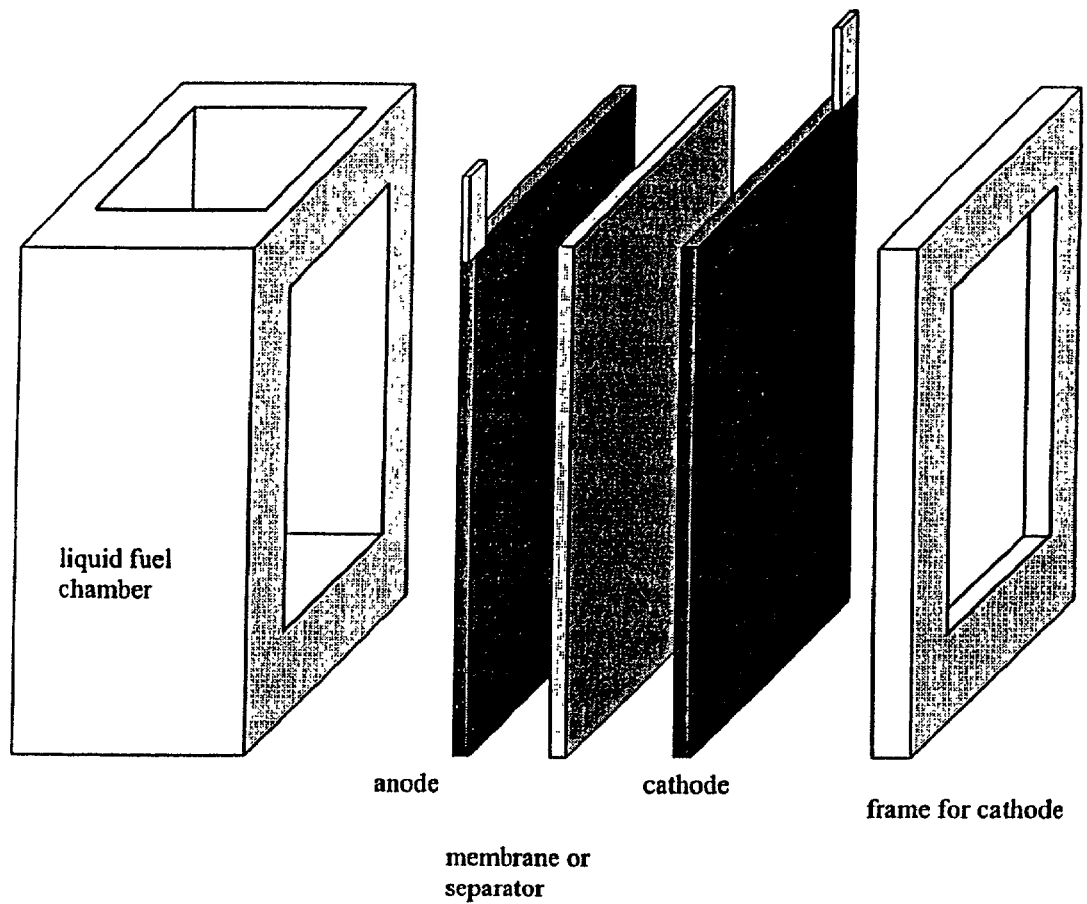
FIG. 9 is a schematic diagram of an exploded view of a test fuel cell.
Figure 10:
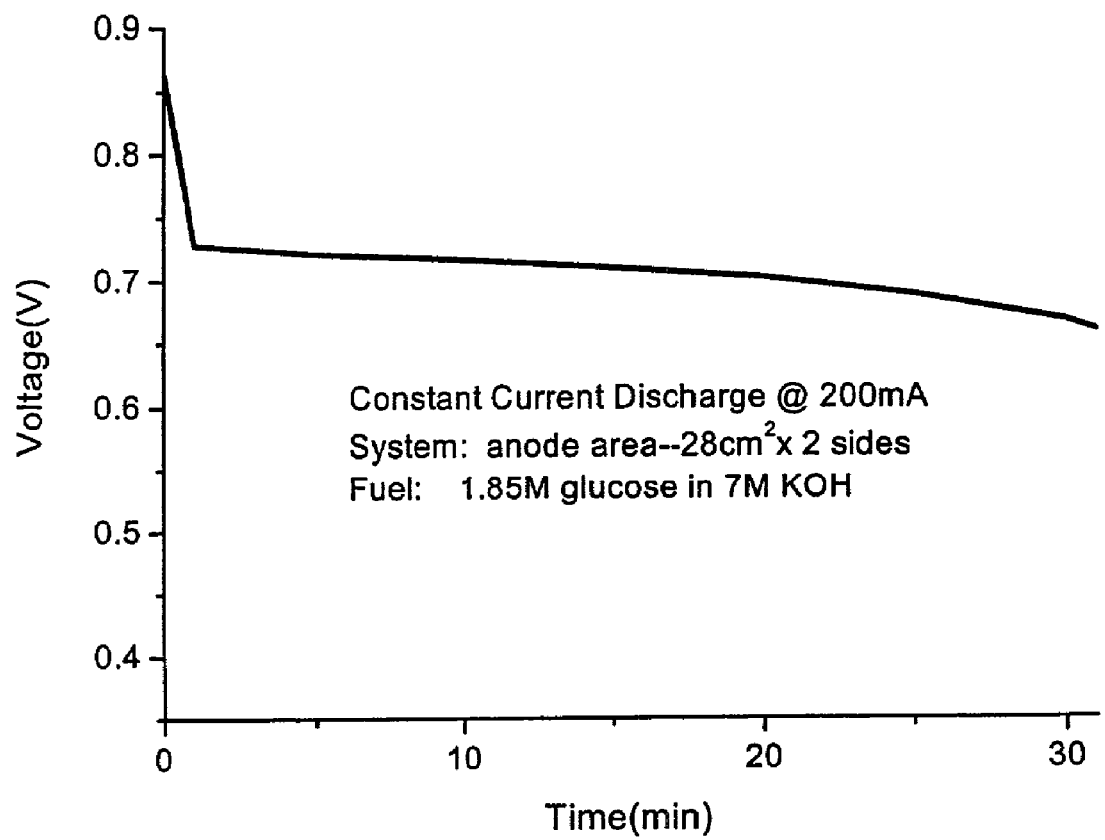
FIG. 10 is a graph showing the discharge characteristics of a room temperature direct glucose-air fuel cell.

The applicability of this invention to a room temperature direct glucose-air fuel cell is now demonstrated. A schematic representation of such a fuel cell is shown in FIG. 9. An anode is prepared in the conventional method by mixing a high surface area carbon such as Vulcan 72, acetylene black with a 2 mg/cm$^2$ loading of Pt and a 1:1 atomic ratio of platinum to cobalt. The cobalt can be applied by electrochemical deposition or codeposition together with platinum from a dissolved chloride salt. The oxides of cobalt are also expected to be present. The cathode used can be a commercially available air cathode, such as Alupower AC65 air cathode with a silver catalyst. Using a 1.0 molar glucose solution in 1.0 molar NaOH, the open circuit voltage of such a glucose-air fuel cell can reach 0.95 V at 22° C. No forced convection of the liquid or air was applied. The current density is 5 mA/cm$^2$ at a cell voltage of 0.4 V at room temperature. A 4 cm×4 cm single cell using a 30 ml volume of the glucose/NaOH solution can turn a small motor fan for 3 hours giving a power density of 0.02 W/g of glucose and 0.05 Whr/g of glucose. Using a more concentrated 7M hydroxide solution, the peak power density improves to 3 mW cm$^{-2}$ or 0.035 W/g of glucose. The discharge of such a fuel cell in 7M KOH solution is shown in FIG. 10. Using a platinum air cathode instead of the AC65 air cathode, the open circuit voltage can reach 1.08 V and power density can increase further. Performance of a room temperature direct glucose-air fuel cell at such a level has never been reported in the literature.

The performance of such a glucose-air fuel cell compares with open literature for conventional methanol-air fuel cells operating at room temperature. Direct methanol-air fuel cells normally uses Pt/Ru as the electrocatalyst and operate above 60° C. A recent report states 20 mW cm$^{-2}$ peak power density at 70° C. in a methanol fuel cell with a pure oxygen flow to the cathode (Amphlett, J. C. et al., 2001, J. Power Sources, 96:204). Normally, an electric heater for preheating the electrolyte is needed for the methanol-air fuel cell. The theoretical open circuit voltage of methanol-air cell is 1.21 V compared to 1.23 V for glucose-air. A 1.08 V open circuit voltage is observed in the room temperature glucose-air cell using the electrocatalyst of this invention but an open circuit voltage below 0.8 is normally reported for the methanol-air fuel cell even at elevated temperatures (Amphlett, J.C. et al., 2001, J. Power Sources, 96:204).

The theoretical energy density of methanol in a methanol-air cell is 17.37 $kJ/cm^3$ but that for glucose is 24.57 $kJ/cm^3$ in a glucose-air cell. Theoretically, the number of electrons for complete electrooxidation of methanol is 6 but for complete oxidation of glucose is 24. In-situ FTIR experiments have detected the strong presence of glucono-lactone and carbon dioxide in the products of electrochemical oxidation of glucose in alkaline and neutral media at relatively low oxidation potentials, as shown in FIG. 6. This demonstrates the effectiveness and intrinsic activity of the electrocatalyst of this invention, although there is room for improvement in the mass-transfer aspect of the electrode design.

The dissolved glucose cross-over effect has been determined to be a 50 to 100 mV lowering of the cathode potential depending on the current density. The activity of platinum-cobalt-oxide electrocatalyst for glucose oxidation is more than an order of magnitude above common catalysts including platinum. This cross-over effect can be minimized with a suitable choice of anionic conducting membrane.

Figure 11:
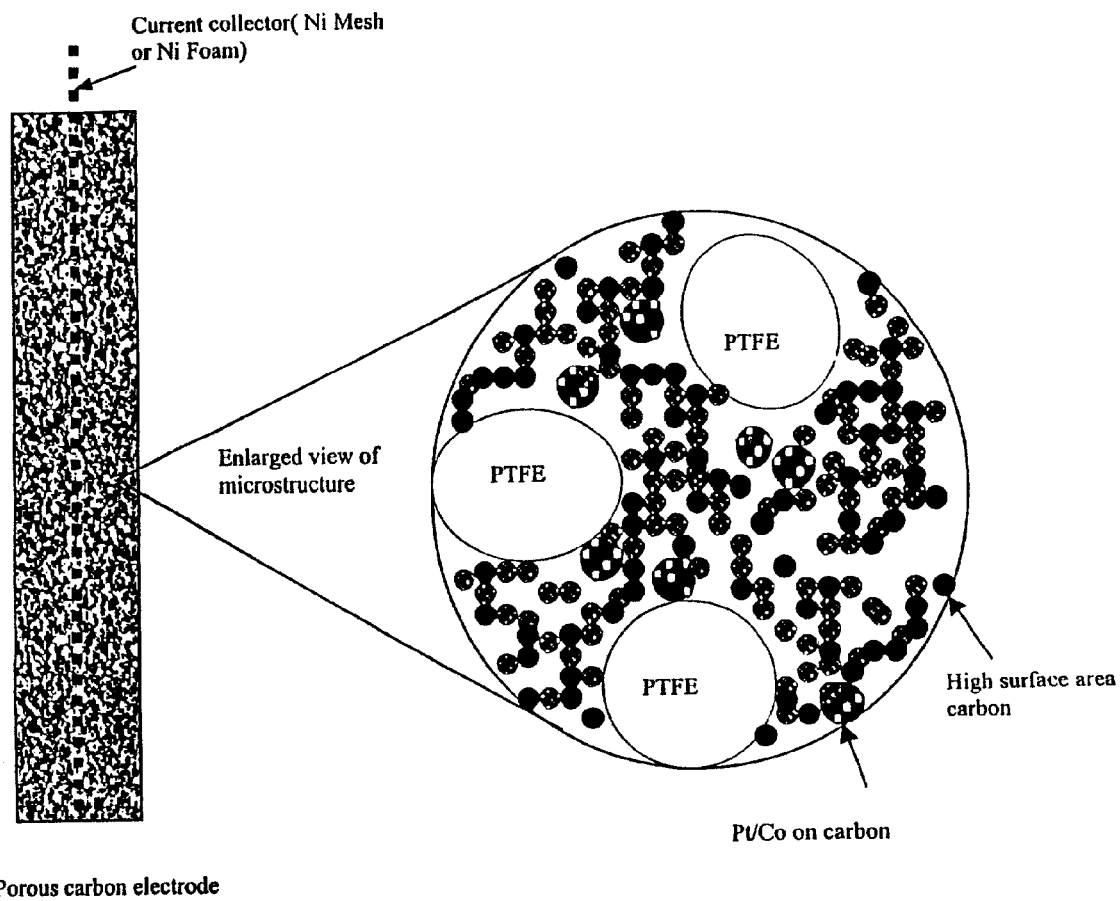
FIG. 11 is a schematic diagram showing the components in the structure of an anode including a hypothetical view of a microstructure containing PTFE.
Figure 12:
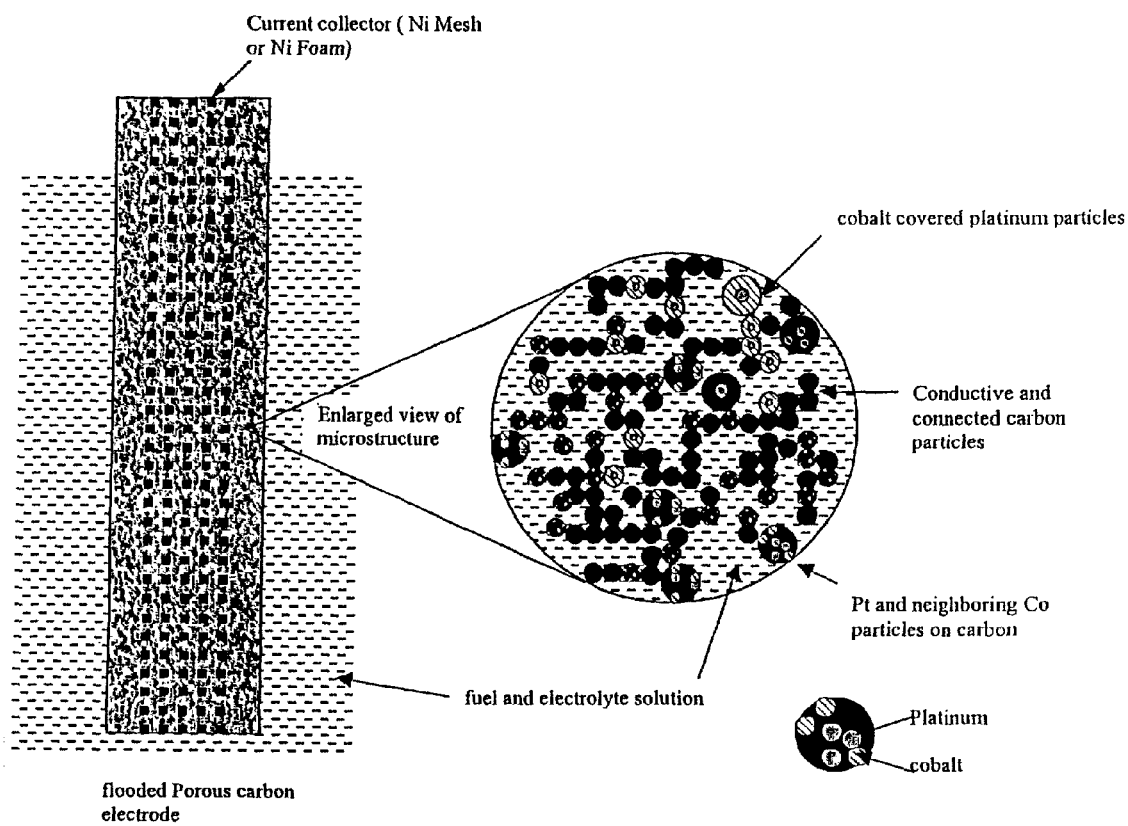
FIG. 12 is a schematic diagram showing the components in the structure of an anode including a hypothetical view of a microstructure containing no PTFE.

The amount of cobalt in the catalyst composition is within the range of about 5 to 70 atom percent of the composition with the balance being Pt. If the amount of Co in the catalyst composition is to be expressed as a weight percent, then the Co is about 1.5 to about 48 weight percent of the catalyst composition, or within the range of about 48 to about 1 weight percent of the total weight of the composition. Likewise, if the amount of Co is to be expressed as an atom ratio, then the Co:Pt atom ratio is within the range of about 1:20 to 3:1. In another embodiment of the invention, the catalyst composition can include tin in addition to platinum and cobalt. If the composition includes tin, then the Co will be in the composition in an amount within the above specified range with the balance of the catalyst composition being a mixture of platinum and tin. The oxidation state of the cobalt in the catalyst composition includes 0, 2, 8/3 or 3, although any oxidation state that provides a catalyst capable of oxidizing glucose may be used. The catalyst composition can be added to electrode forming materials to create a composite electrode or the catalyst composition can be supported on various support structures such as a metal wire (shown schematically in FIG. 2), metal electrode, metal foam (shown schematically in FIGS. 11, 12), graphite electrode, a porous carbon electrode or a gas diffusion electrode.

In another embodiment, the electroctalyst of the invention can be used to synthesize gluconic acid from a glucose solution. Gluconic acid is produced as a product during the oxidation of glucose. The electrocatalyst can therefore be employed to catalyze the oxidation of glucose to gluconic acid and the gluconic acid can be recovered from the solution.

The electrocatalyst in this invention can be prepared by several methods including impregnation, gas phase or solution phase chemical reduction, electrodeposition, vapour deposition, and electrochemical reactive deposition. The complete mixing of the different metals to form an alloy is not necessary to prepare the catalyst of the present invention. For example, the Co can be layered onto a supporting structure such as a Pt wire electrode like the one shown in FIG. 2. The Co can be added as an outside layer or the Co can be added side-by-side with Pt onto a wire electrode. Likewise, the Co can be added as an outside layer or side-by-side to an existing Pt and carbon structure. Some examples are described below.

EXAMPLE 1

A wire electrode with the electrocatalyst Pt/Co/$Co_3O_4$ giving the results shown in FIG. 1(*b*) was prepared as follows. Platinum and cobalt were co-deposited on a platinum wire of 0.5 mm diameter from a mixed solution of 0.3 molar $CoCl_6.6H_2O$ and 0.032 molar chloroplatinic acid in deionized water (see FIG. 2 for schematic diagram of layered wire electrode). The immersed depth of the working electrode was 1 cm. A three-electrode cell was used with a platinum foil as the counter electrode and a saturated calomel electrode (SCE) as the reference electrode. Oxygen bubbles were introduced from a cylinder to impinge on the wire electrode so that reactive deposition forming cobalt oxides of CoO(OH), $Co_3O_4$, and $Co_2O_3$ occurred. The details of reactive deposition to produce oxides of cobalt with high surface area are described in the literature (Jiang, S. P. et al, 1990, Electrochem. Soc. 137:3374). The deposition was controlled galvanostatically at 17 $mA/cm^2$ for 300 seconds and the rate of bubbling oxygen was about 3 ml/min. Under this preparation, most of the cobalt oxides formed are in the form of $Co_3O_4$ with an oxidation state of 8/3.

EXAMPLE 2

An anode carrying the electrocatalyst of this invention is prepared from a carbon electrode (ELAT electrodes from E-TEK Corp, New Jersey) by electrodeposition in a 0.04 molar $H_2PtCl_6$ and 0.098 molar $CoCl_2$ solution at 50 mA $cm^{-2}$ for 30 minutes. The resulting surface is analyzed to have 85.1 atom % Pt, 14.6 atom % Co and 0.3atom % Cl by EDX analyses. X-ray photoelectron spectroscopy indicated the oxidation state of cobalt is zero. The surface morphology is shown in FIG. 6 with appreciable roughness. The performance of this anode for the oxidation of 0.5 molar glucose in 0.5 molar NaOH is shown in FIG. 7.

EXAMPLE 3

Figure 13:
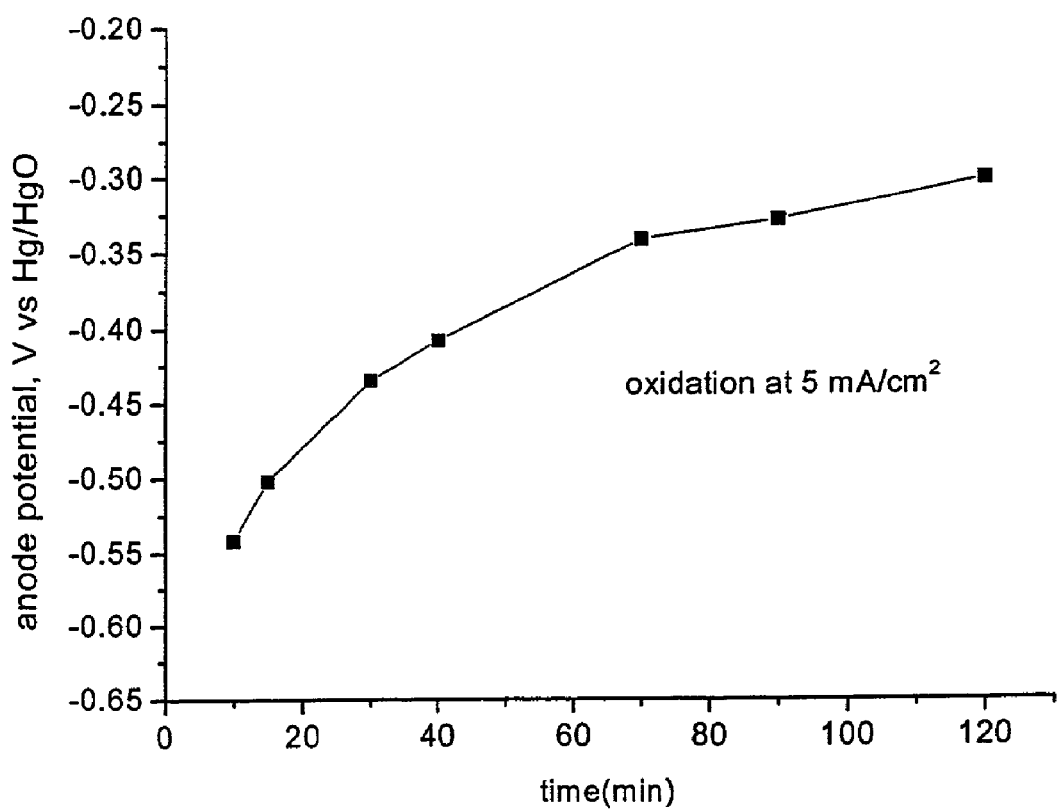
FIG. 13 is a graph showing the performance of an Pt/Co/C anode prepared by chemical reduction.

An anode carrying the electrocatalyst of this invention is prepared by a chemical reduction method. Vulcan 72 activated carbon was added to a solution containing 40 mM hexachloroplatinic acid and 120 mM cobalt acetate in a ratio of 1 g to 50 ml. Excess hydrazine was added to reduce the platinum and cobalt. The carbon is used to make a paste with acetylene black and 60% polytetrafluoroethylene (PTFE) aqueous emulsion in the ratio of 70%, 10%, and 20% by weight respectively. The paste is applied to a piece of 1.5 mm thick, 400 g $m^{-2}$ nickel foam. FIG. 13 shows the performance of a Pt/Co/C anode prepared by chemical reduction. The electrochemical oxidation of 0.5 molar glucose oxidation in 0.5 molar NaOH at 5 mA $cm^{-2}$ is shown in FIG. 13 (i.e., the anodic oxidation is 0.5 M glucose in 0.5 M NaOH at 5mA $cm^{-2}$ at 20° C.).

EXAMPLE 4

A glucose fuel cell anode carrying the electrocatalyst of this invention is prepared with a common method of making a porous electrode as follows. An activated carbon with 10% Pt loading from Heraeus Co. was the source of the Pt. The Pt particles have a narrow size distribution of 1.5 to 3.0 nm. Six grams of this powder was mixed uniformly with 0.224 g of acetylene black and 1.2 g aqueous emulsion of PTFE (60% by weight) and ethanol with continuous stirring to make a paste. 0.38 gram of the paste was then applied to a 4 cm×7 cm 400 g $m^{-2}$ nickel foam which serves as the current collector (nickel mesh could also be used as the current collector). A small amount of cobalt was electrochemically deposited to the electrode. A 10:90 dried weight ratio of PTFE to catalyst was used in this example (Alternatively, the PTFE could be replaced by a hydrophilic ("wetting") binder, or not be present at all). The electrode is a "flooded" electrode without the presence of gas or a gas-liquid interface. The electrode is completely immersed in the liquid fuel and electrolyte solution. The performance of such an anode is demonstrated in a glucose-air fuel cell using two Alupower AC-65 air breathing cathodes of either side of the anode. The total surface area is therefore 56 cm$^2$. The fuel is 6 ml of a 1.85 molar glucose in 7 molar KOH. The discharge behavior at a current of 200 mA of the cell at 20° C. is shown in FIG. 10. The starting power is above 3 mW cm$^{-2}$ and the average power density in the first 20 minutes is 2.5 mW cm$^{-1}$. Using a 0.6 mg cm$^{-2}$ platinum loading cathode and an anionic membrane, the open circuit voltage can reach above 1.08 V at room temperature.

EXAMPLE 5

Figure 14:
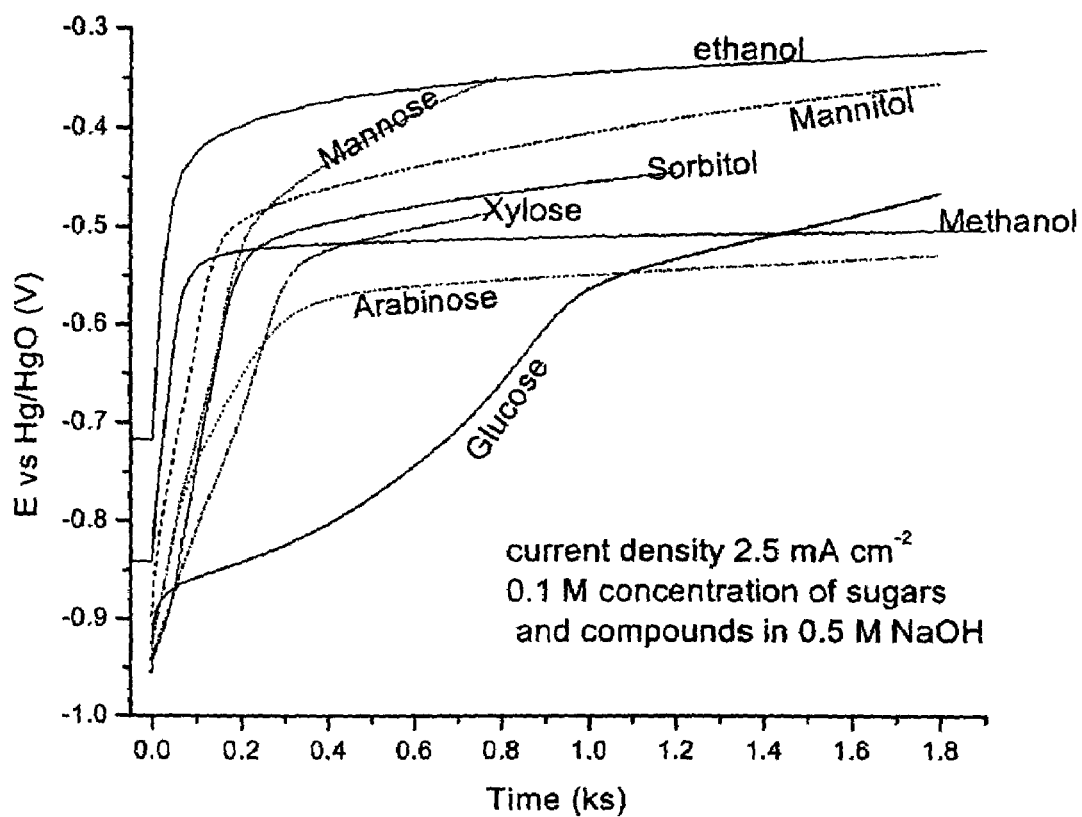
FIG. 14 is a graph showing a comparison of the constant current oxidation of different sugars and compounds on a Pt/Co anode.

FIG. 14 shows a comparison of the constant current oxidation of different sugars and compounds on a Pt/Co anode. The electrochemical oxidation of other carbohydrates and related compounds is demonstrated with an anode prepared as follows. A platinum disk as a cathode is immersed in a solution of 0.045 molar $H_2PtCl_6$ and 1 molar $CoCl_2$ solution and a deposition current of 2.5 mA cm$^{-2}$ was passed for 30 minutes. The electrode is then used as an anode for half cell studies of oxidation of various sugars and compounds in 0.5 M NaOH. The resulting chronopotentiograms are shown in FIG. 14.

Although preferred embodiments of the invention have been shown and described, it should be understood that various modifications and substitutions, as well as rearrangements and combinations, can be made by those skilled in the art, without departing from the spirit and scope of this invention.

REFERENCES

[1] G. G. Neuburger, D. C. Johnson, Anal. Chem., 59 (1987) 150.
[2] I. T. Bae, X. Xing, C. C. Liu, and E. Yeager, X. Xing, and C.C. Liu, J. Electroanal. Chem., 284 (1990) 335.
[3] Y. B. Vassilyev, O. A. Khazova, and N. N. Nikolaeva, J. Electroanal. Chem., 196 (1985) 105, 127.
[4] S. V. Prabhu and R. P. Baldwin, Anal. Chem., 61 (1989) 852.
[5] J. Wang and Z. Taha, Anal. Chem., 62 (1990) 1413.
[6] R. F. Reim and R. M. Van Effen, Anal. Chem., 58 (1986) 3203.
[7] L. M. Santos and R. P. Baldwin, Anal. Chim. Acta, 206 (1988) 85.
[8] J. Zhou and E. Wang, J. Electroanal. Chem., 331 (1992) 1029.
[9] X. Zhang, K. Y. Chan, and A. C. C. Tseung, J. Electroan. Chem., 386 (1995) 241.
[10] X. Zhang, K. Y. Chan, J. K. You, Z. G. Lin, and A. C. C. Tseung, J. Electroan. Chem., 430 (1997) 147.
[11] B. Wan and A. C. C. Tseung, Biomed. Eng. Jan (1974) 14
[12] T. Chen, S. C. Barton, G. Binyamin, Z. Gao, Y. Zhang, H-H Kim, and A. Heller, J. Am. Chem. Soc., (2001) in press.
[13] J. C. Amphlett, B. A. Peppley, E. Halliop, and A. Sadiq, J. Power Sources, 96 (2001) 204.
[14] S. P. Jiang, Y. Z. Chen, J. K. You, T. X. Chen, and A. C. C. Tseung, J. Electrochem. Soc. 137 (1990)3374.

The invention claimed is:
1. A method comprising:
catalyzing, with a catalyst, electrochemical oxidation of organic molecules in liquid solution, the catalyst com-

TABLE 1

Comparison of electrocatalysts for glucose oxidation.

| Reference | Electrocatalyst | Electrolyte | Oxidation Potential | Current Density |
|---|---|---|---|---|
| Neuburger & Johnson [1] | gold | 0.2 M NaOH | 0.4 V Ag\|AgCl | 0.02 mA/cm$^2$ |
| Bae et al. [2] | platinum | 0.1 M HClO$_4$ | 0.0 V/SCE | 0.05 mA/cm$^2$ |
| Vassilyev et al. [3] | rhodium | PH 7.2 buffer | 0.6 V RHE | 0.01 mA/cm$^2$ |
| Vassilyev et al. [3] | iridium | PH 7.2 buffer | 0.4 V RHE | 0.02 mA/cm$^2$ |
| Prabhu and Baldwin [4] | Copper CME | 0.15 M NaOH | 0.4 V Ag\|AgCl | 0.4 mA/cm$^2$ |
| Wang and Taha [5] | RuO$_2$ | 1 M NaOH | 0.4 V Ag\|AgCl | 0.2 mA/cm$^2$ |
| Reim and Van Effen [6] | Nicket(III) Oxide | 0.15 M NaOH | 0.45 V Ag\|AgCl | 0.2 μA/cm$^2$ |
| Santos and Baldwin [7] | CoPC | 0.15 M NaOH | 0.4 V Ag\|AgCl | 0.5 μA/cm$^2$ |
| Zhou and Wang [8] | Prussian Blue CME | 0.5 M KCl | 0.4 V SCE | 0.2 μA/cm$^2$ |
| Zhang et al. [9, 10] | Pt\|WO$_3$ | 0.5 M H$_2$SO$_4$ | 0.0 V/SCE | 6 mA/cm$^2$ |
| This invention | Pt\|Co\|O\|C | 0.5 M NaOH | −0.80 V/Hg/HgO | 5 mA/cm$^2$ |

TABLE 2

Comparison of glucose-air or glucose-oxygen fuel cells.

| Reference | Electrocatalyst | Electrolyte | Power Density | Temperature |
|---|---|---|---|---|
| Wan and Tseung [11] | Platinum black | 0.5 M NaCl | 20 μW/cm$^2$ <br> 3.3 μW/(in vivo) | 37° C. |
| Chen et al. [12] | Glucose oxidate and Osmium complex | Citrate buffer pH 5 | 64 μW/cm$^2$ <br> 137 μW/cm$^2$ | 23° C. <br> 37° C. |
| This invention | Pt\|Co\|O\|C | 7 M KOH | 3 mW/cm$^2$ | 20° C. | prising a mixture of platinum, cobalt in an amount of about 1 to about 48% by weight of the catalyst, and tin.

2. The method as defined in claim 1 wherein said catalyst is supported on an electrode.

3. The method of claim 1 wherein said platinum is present in an amount within the range of about 52 to about 99 weight percent of the catalyst.

4. The method of claim 1 wherein said cobalt is present in an oxidation state of 0, 2, 8/3 or 3.

5. The method of claim 1 wherein said catalyst further comprises a mixture of carbon and polytetrafluoroethylene.

6. The method of claim 1 wherein the platinum and the cobalt are mutually discrete.

7. The method of claim 6 wherein the platinum and the cobalt are in the form of platinum particles and cobalt particles.

8. The method of claim 1 wherein the organic molecules are glucose molecules.

9. The method of claim 1 wherein the oxidation of the organic molecules uses the organic molecules as fuel for a fuel cell.

10. The method of claim 8 wherein the oxidation converts the glucose molecules to gluconic acid.

11. The method of claim 1 wherein the tin is not greater than about 10 atom percent of the catalyst.

12. The method of claim 1 wherein the catalyst is part of an electrode.

13. The method of claim 1 wherein the electrode functions as an anode in the catalyzing step.

14. The method of claim 1 wherein the cobalt is about 1.5 to about 48% by weight of the catalyst.

15. A method comprising:
    catalyzing, with a catalyst, electrochemical oxidation of glucose in liquid solution, the catalyst comprising a mixture of platinum, cobalt in an amount of about 1.5 to about 48% by weight of the catalyst, and tin.

16. The method as defined in claim 15 wherein said catalyst is supported on an electrode.

17. The method of claim 15 wherein said platinum is about 52 to about 99 weight percent of the catalyst.

18. The method of claim 15 wherein the platinum and the cobalt are in the form of platinum particles and cobalt particles.

19. The method of claim 15 wherein the oxidation uses the glucose as fuel for a fuel cell.

20. The method of claim 15 wherein the tin is not greater than about 10 atom percent of the catalyst.

21. The method of claim 15 wherein the catalyst is part of an electrode.

* * * * *